United States Patent
Ahlberg et al.

(10) Patent No.: US 9,289,213 B2
(45) Date of Patent: Mar. 22, 2016

(54) MULTIPLE CLIP APPLIER APPARATUS AND METHOD

(71) Applicant: Applied Medical Resources Corporation, Rancho Santa Margarita, CA (US)

(72) Inventors: Russell E. Ahlberg, Rancho Santa Margarita, CA (US); Steven R. Anderson, Las Flores (CA); Edward E. Dolendo, Mission Viejo, CA (US); Vincent C. Tangherlini, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 198 days.

(21) Appl. No.: 14/022,899

(22) Filed: Sep. 10, 2013

(65) Prior Publication Data

US 2014/0012291 A1    Jan. 9, 2014

Related U.S. Application Data

(63) Continuation of application No. 10/381,970, filed as application No. PCT/US01/31160 on Oct. 4, 2001, now Pat. No. 8,529,588.

(60) Provisional application No. 60/238,723, filed on Oct. 6, 2000.

(51) Int. Cl.
| | |
|---|---|
| *A61B 17/04* | (2006.01) |
| *A61B 17/10* | (2006.01) |
| *A61B 17/128* | (2006.01) |

(52) U.S. Cl.
CPC ............. *A61B 17/105* (2013.01); *A61B 17/128* (2013.01)

(58) Field of Classification Search
CPC .. A61B 17/105; A61B 17/128; A61B 17/068; A61B 2017/07271; A61B 2017/07278; A61B 17/07207
See application file for complete search history.

(56) References Cited

U.S. PATENT DOCUMENTS

| 2,420,830 A | 5/1947 | Maynard |
| 4,226,242 A | 10/1980 | Jarvik |

(Continued)

FOREIGN PATENT DOCUMENTS

| EP | 0 112 980 | 7/1984 |
| WO | WO 00/42922 | 7/2000 |

OTHER PUBLICATIONS

European Patent Office, Supplementary European Search Report for European Patent No. 01 97 9480, having an International Application No. of PCT/US01/31160, dated Mar. 5, 2007.

(Continued)

*Primary Examiner* — Gregory Anderson
(74) *Attorney, Agent, or Firm* — John F. Heal

(57) ABSTRACT

A surgical clip applier includes a train of clips disposed in a plane with a single clip removed from the train of clips and disposed in a staging position. A pair of jaws are adapted to receive the single clip from the staging position by operation of a jaw loader moveable outside the plane of the train of clips. In an associate method, a handle assembly is provided which is moveable in an open stroke and a closed stroke. A source of surgical clips are provided along with a pair of jaws which are adapted to receive one of the clips as the handle assembly is moved in an open stroke, the jaws are open to receive the clip. Following the opening of the jaws, a jaw loader is extended to a position between the jaws to move the clip into the jaws. The handle assembly is moveable in a closed stroke during which the jaws are closed to crimp the clip. Prior to this closing of the jaws, the jaw loader is retracted from the position between the jaws leaving the clip in the jaws.

17 Claims, 16 Drawing Sheets

(56) References Cited

U.S. PATENT DOCUMENTS

| | | | |
|---|---|---|---|
| 4,296,751 A | 10/1981 | Blake et al. | |
| 5,423,835 A | 6/1995 | Green et al. | |
| 5,700,270 A | 12/1997 | Peyser et al. | |
| 5,720,756 A * | 2/1998 | Green et al. | 606/143 |
| 6,599,298 B1 | 7/2003 | Forster et al. | |

OTHER PUBLICATIONS

Co-Pending U.S. Appl. No. 11/021,852, filed Dec. 23, 2004. Title: Surgical Instrument With Improved Handle Assembly.

Co-Pending U.S. Appl. No. 11/536,467, filed Sep. 28, 2006. Title: Manually Actuated Surgical Clip Applier.

Co-Pending U.S. Appl. No. 11/039,188, filed Jan. 19, 2005. Title: Single Fire Vascular Clip Applier With Disposable Jaw.

Co-Pending U.S. Appl. No. 10/518,436, filed Dec. 16, 2004. Title: Clip Applier Cartridge With Internal Ratchet.

Co-Pending U.S. Appl. No. 10/815,149, filed Mar. 30, 2004. Title: Convertible Surgical Clip Applier System.

* cited by examiner

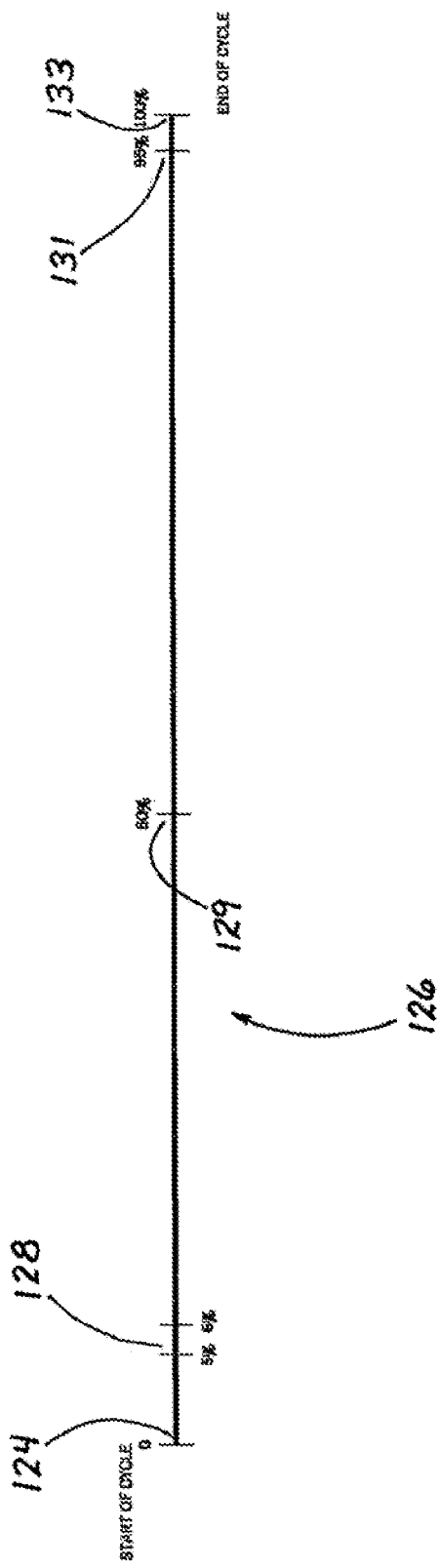

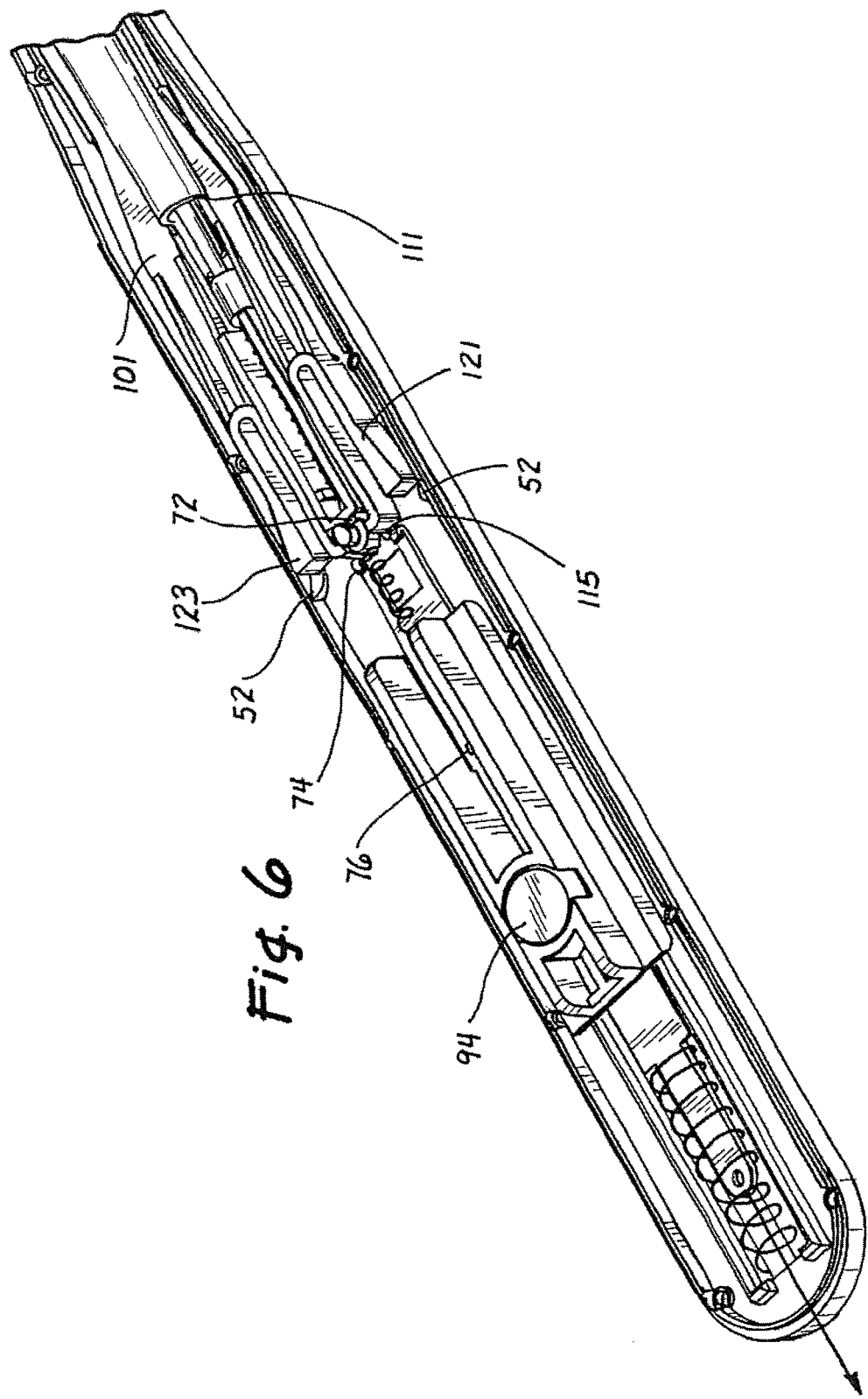

MULTIPLE CLIP APPLIER APPARATUS AND METHOD

CROSS REFERENCE TO RELATED APPLICATIONS

This application is a continuation of U.S. patent application Ser. No. 10/381,970, entitled "MULTIPLE CLIP APPLIER APPARATUS AND METHOD," which entered the national stage under 35 U.S.C. §371 on Mar. 5, 2004, currently pending, which is a national stage entry of PCT Application No. PCT/US01/31160, entitled "MULTIPLE CLIP APPLIER APPARATUS AND METHOD," filed Oct. 4, 2001, which claims the benefit of U.S. Provisional Application Ser. No. 60/238,723, entitled "MULTIPLE CLIP APPLIER APPARATUS AND METHOD," filed on Oct. 6, 2000. Each of these applications is incorporated by reference in its entirety.

Related subject matter can be found in PCT application No. PCT/US00/01296 filed on Jan. 19, 2000 and entitled "Modular Ligating Apparatus and Method", and also U.S. Provisional Patent Application No. 60/117,079 filed on Jan. 25, 1999 and entitled: "Modular Ligating Apparatus and Method." Each of these applications is incorporated by reference in its entirety.

BACKGROUND OF THE INVENTION

Clip appliers of the past have included cartridges containing multiple clips. These cartridges have been automatically actuated and accordingly have not offered the tactical feedback desired by surgeons. In addition, automatic clip appliers have been exceedingly complex typically requiring not less than 22 moving parts. Tactical feedback is appreciated as it gives a surgeon some indication as to the amount of force being applied by the clip to the body tissue, such as a blood vessel. Only single clip appliers have provided this tactical feedback.

Multiple clip appliers have used jaw loaders to individually load each clip, into the jaws of the applier. Removing the jaw loaders from between the jaws prior to crimping the clip has sometimes resulted in jamming.

SUMMARY OF THE INVENTION

In accordance with the present invention, a multiple clip applier is disclosed which provides a high degree of tactical feedback with only six moving parts. The resulting applier provides the desired feedback with a relatively simple mechanisms and a high degree of reliability.

A mechanical delay circuit is disclosed which loads a clip only in the last five (5) percent of the opening stroke and removes the clip loader in the first five (5) percent of the closing stroke. These steps of loading and removing are accomplished in a positive, substantially instantaneous manner. The resulting efficiency, reliability, disposability, alignment, tactical feedback, and repeatable operation can all be appreciated within the scope of this invention.

These and other features and advantages of the invention will be better understood with a description of preferred embodiments and reference to the associated drawings.

DESCRIPTION OF THE DRAWINGS

FIG. 5b is a time line showing the sequence of operation in a preferred embodiment of the invention;

FIG. 6 is a top-side perspective view of a slide block retractor and jaw loader mechanism relatively positioned at the beginning of a retraction stage;

DESCRIPTION OF PREFERRED EMBODIMENTS

Figure 1:
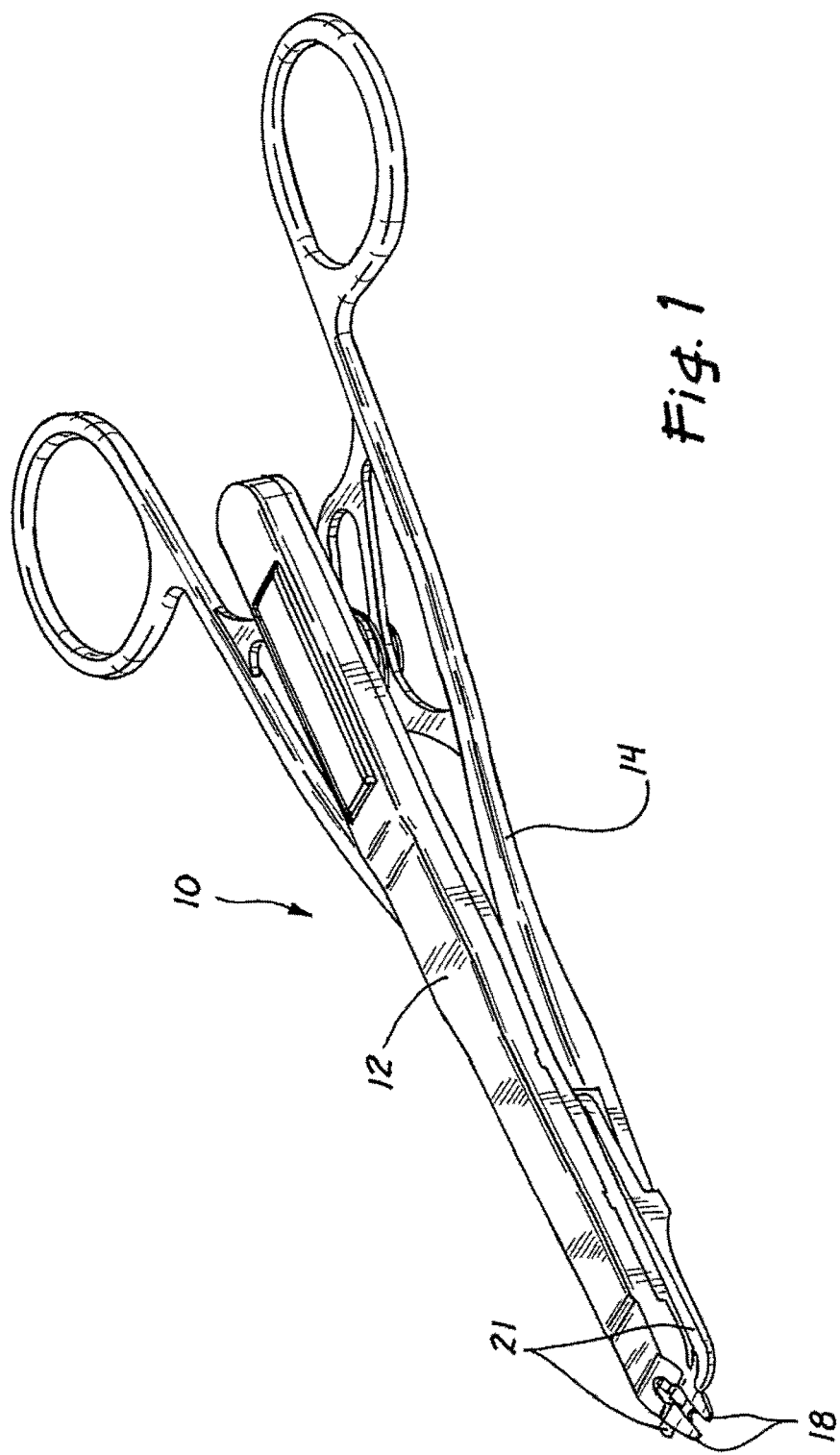
FIG. 1 is a top-side perspective view of one embodiment of the clip applier of the present invention.
Figure 2:
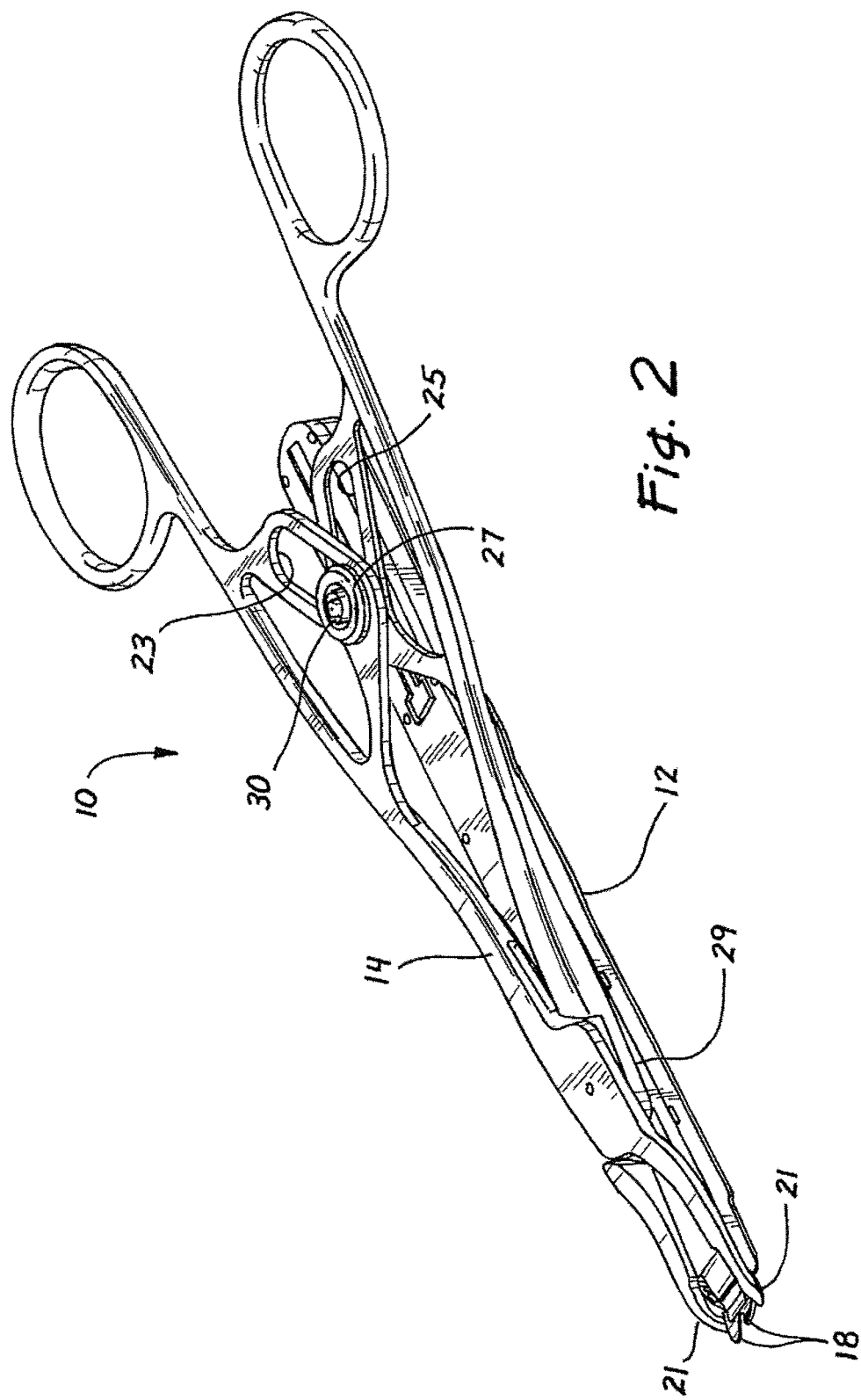
FIG. 2 is a bottom side perspective view of the clip applier illustrated in FIG. 1.
Figure 3:
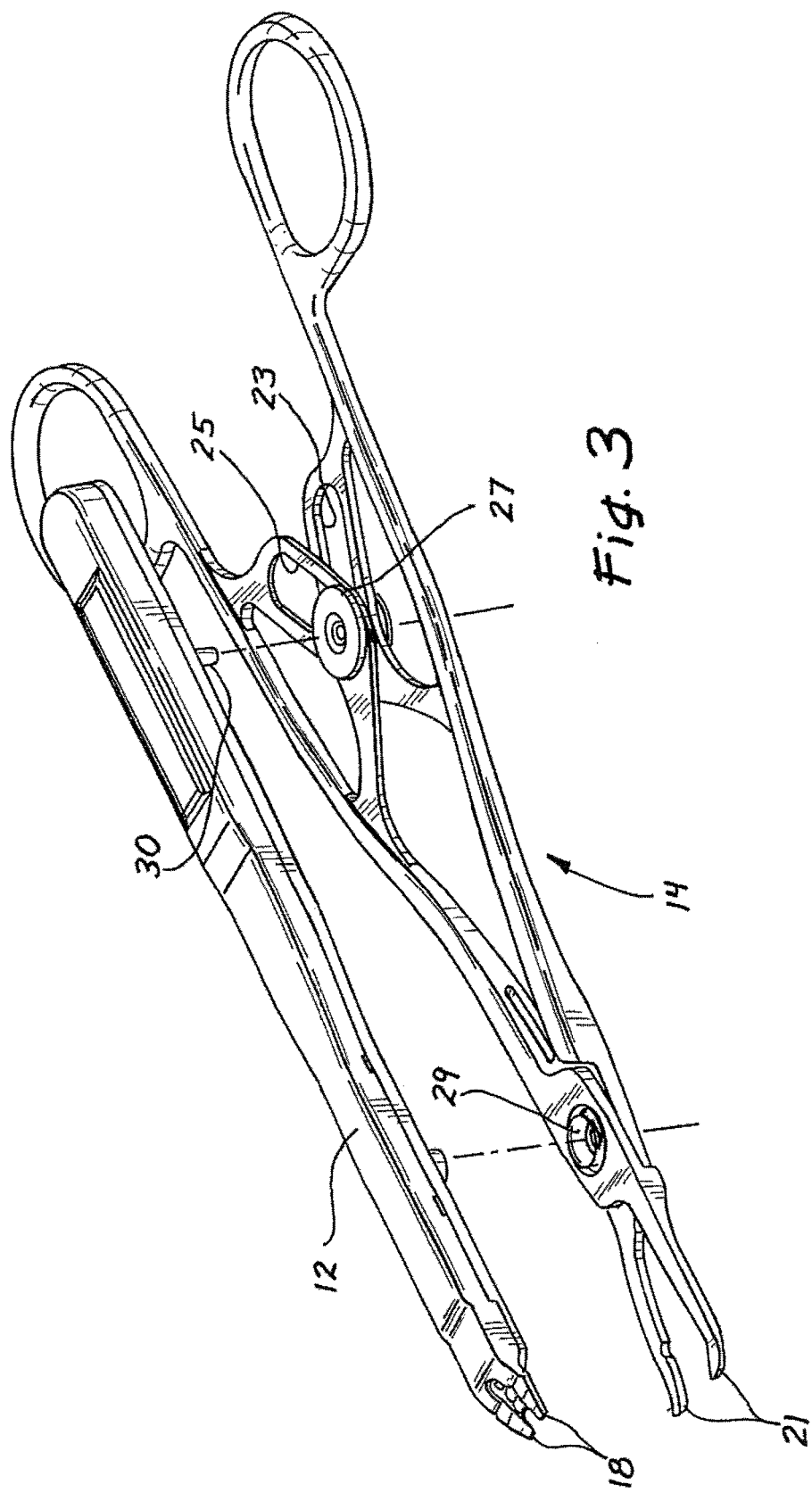
FIG. 3 is an exploded view of the clip applier showing a disposable clip cartridge removed from a snap-fit relationship with a handle assembly.

A multiple-clip clip applier of the present invention is illustrated in FIG. 1 and designated by the reference numeral 10. The clip applier 10 includes a disposable cartridge 12, and a non-disposable handle assembly 14 which can be coupled to the cartridge 12 in a snap-fit relationship as illustrated in FIG. 1 At a distal end 16 of the applier 10, the cartridge 12 is provided with metal jaws 18 which are disposable with the cartridge 12. The jaws 18 are biased to an open state but moveable to a closed state. The handle assembly 14 has a scissors configuration and a pair of pawls 21 at the distal end 16 which can be moved together to close the jaws 18, and can be moved apart to permit the jaws 18 to open. The self alignment of the jaws 18 is of particular advantage to the present invention and generally guaranteed with the replacement of each disposable cartridge 12. This self alignment of the jaws 18 is disclosed in greater detail in PCT Application Serial No. PCT/US00/01216. This alignment of the jaws 18 is independent of the alignment or misalignment of the pawls 21 as disclosed in greater detail in U.S. Patent Application Ser. No. 60/117,079. This latter application also discloses operation of the handle assembly 14 which includes a pair of converging slots 23 and 25, best illustrated in the bottom view of FIG. 2. The handle assembly 14 is operable like a pair of scissors with an opening stroke and a closing stroke. A button 27 rides within the converging slots 23, 25 between a distal position associated with the end of the opening stroke and a proximal position associated with the end of the closing stroke.

The cartridge 12 in this embodiment is snap-fit to the handle assembly 14 at a fulcrum 29 and also through a cartridge drive pin 30 at the button 27. This snap-fit relationship is best illustrated in the assembly view of Figure.

Figure 4:
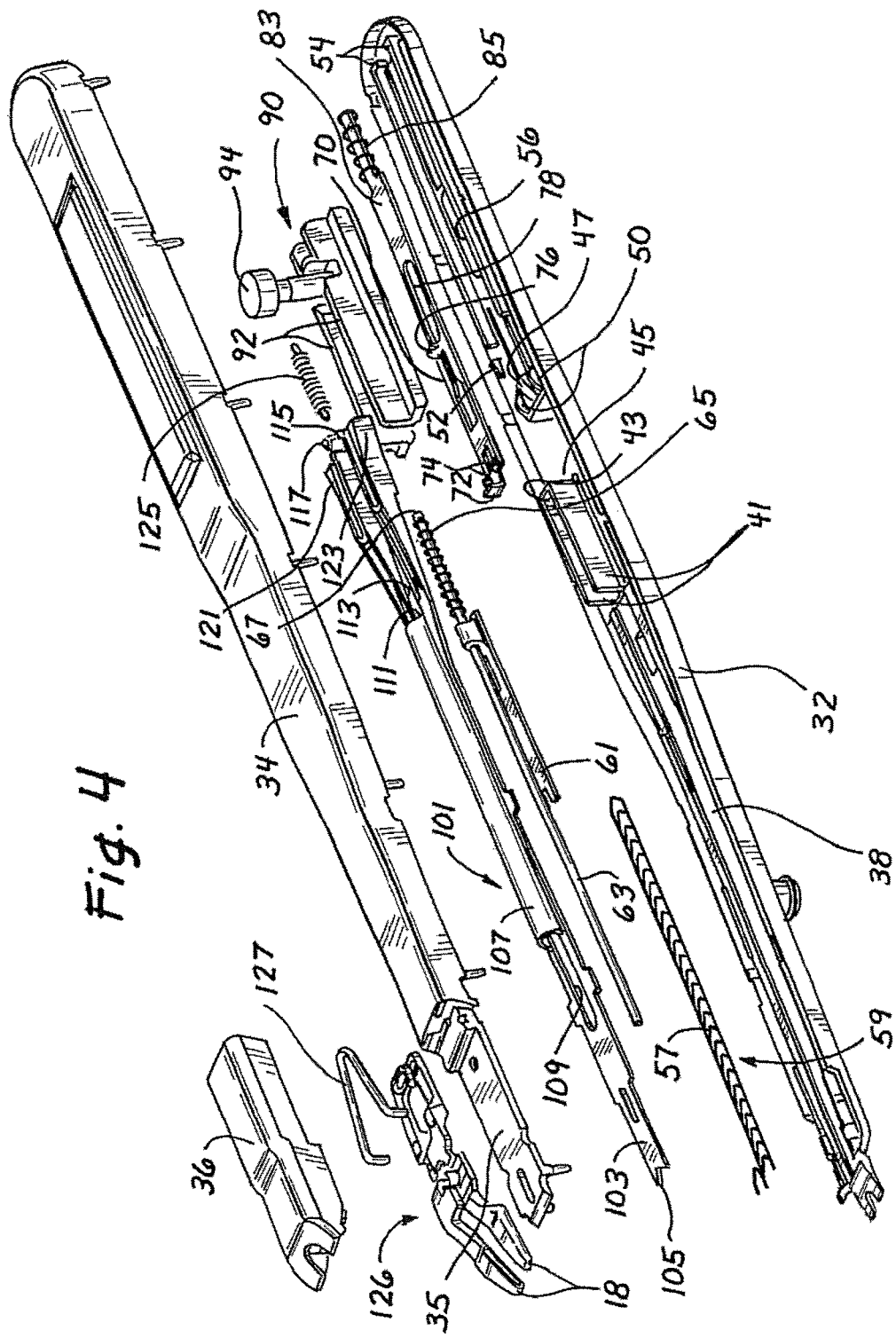
FIG. 4 is an exploded view of one embodiment of the cartridge associated with the present invention.

FIG. 4 shows an exploded view of the cartridge 12 which in this case includes a bottom housing 32, a top housing 34 with a platform 35, and a housing cap 36. The bottom housing 32 includes a clip train channel 38 and a pair of upstanding walls 41 terminating proximally in a ball housing 43 and a wall 45. The bottom housing also includes a keeper 47, having a pair of ramped actuators 50. A pair of inclined elements 52 are also provided along with distal walls 54 and a drive pin slot 56.

The cartridge 12 is initially assembled by placing a plurality of clips 57 into the channel 38. In this embodiment, the clips 57 are aligned end-to-end to form a clip train 59. The clip train 59 is biased in the distal direction by a clip advancer 61 which rides within the channel 38. The advancer 61 moves along a rod 63 and is biased distally by a spring 65. At the proximal end of the rod 63, a ball or enlargement 67 is formed and seated in a fixed relationship with the ball housing 43.

A retractor 70 moves along the bottom housing 32 and includes an upstanding tab 72, a pair of abutments 74, an inclined tab 76, a drive pin slot 78, and a tongue 81 extending from a pair of shoulders 83. A compression spring 85 is mounted on the tongue 81 and is compressed between the shoulders 83 and the upstanding walls 54.

A slide block 90 is disposed over the retractor 70 and includes a pair of upstanding walls which define a longitudinal slot configured to receive the inclined tab 76. A drive pin 94 is seated in the block 90 and extends through the slot 78 in the retractor 70, as well as the slot 56 in the bottom housing 32.

A jaw loader 101 is of particular interest to the present invention. It includes a distally extending tongue 103 terminating in a V-slot 105 which is complimentary in shape to the clips 57. Proximally of the tongue 103, a tunnel 107 is formed over a slot 109 which is shaped to receive the clip advancer rod 63. The tunnel 107 terminates at a proximal surface 111. Proximally of this surface 111, an axial slot 113 extends to a proximal wall 115 which includes a spring tab 117. Outwardly of the slot 113, a pair of wings 121 and 123 are provided with a leaf spring configuration. In its assembled state, the tab 72 of the retractor 70 is disposed within the slot 113 distally of the wall 115. The jaw loader 101 is positioned distally of the slide block 90 with a tension spring 125 disposed between the walls 92 and attached at opposite ends to the spring tab 117 on the jaw loader 101 and the inclined tab 76 on the retractor 70.

The top 34 registers with the bottom 32 to form a housing of the cartridge 12. The top 34 also provides the platform 35 to receive the jaws 18 and their associated alignment assembly 126 and jaw spring 127. The cap 36 forms a cover over this platform 35.

Operation of the cartridge 12 involves two generally separate and independent mechanisms: (1) a continuous and ongoing mechanism for advancing the clip train 59, and (2) a delay mechanism for loading the next clip into the jaws.

Figure 5A:
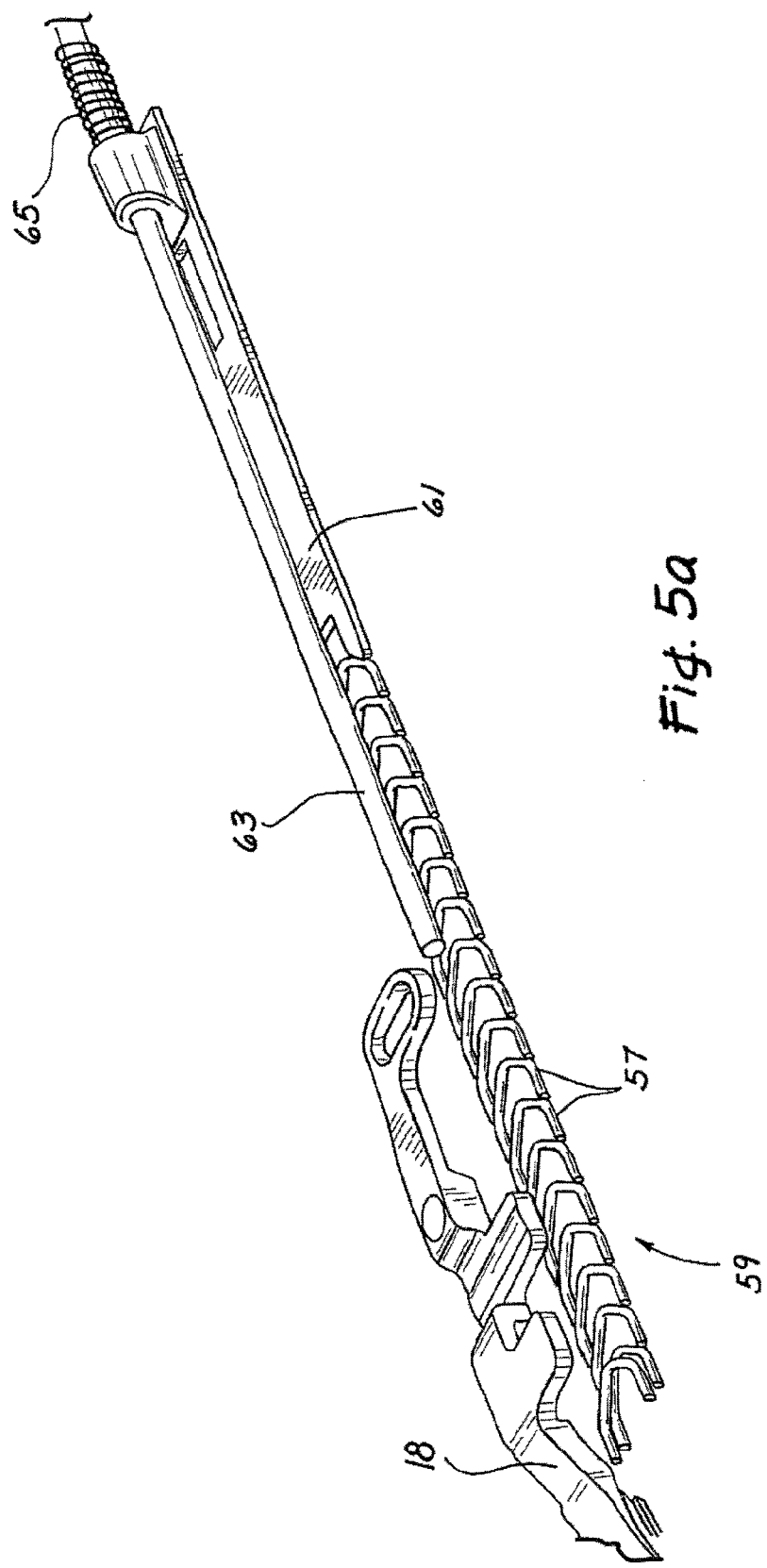
FIG. 5a is a top-side perspective view of a clip train and clip advancer mechanism.
Figure 7:
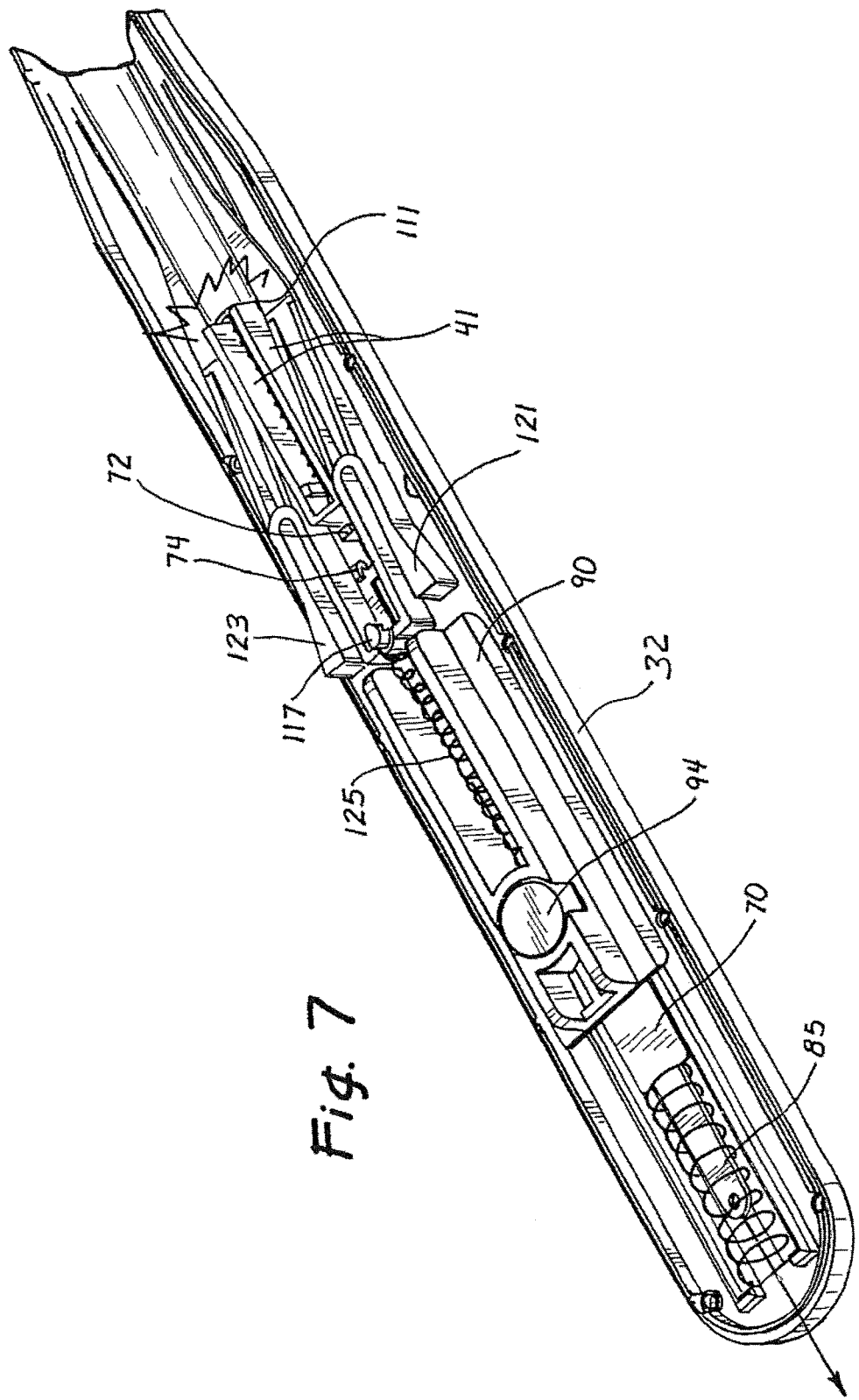
FIG. 7 is a top-side perspective view of the retractor slide block and jaw loader showing the jaw loader in a retracted position.
Figure 8:
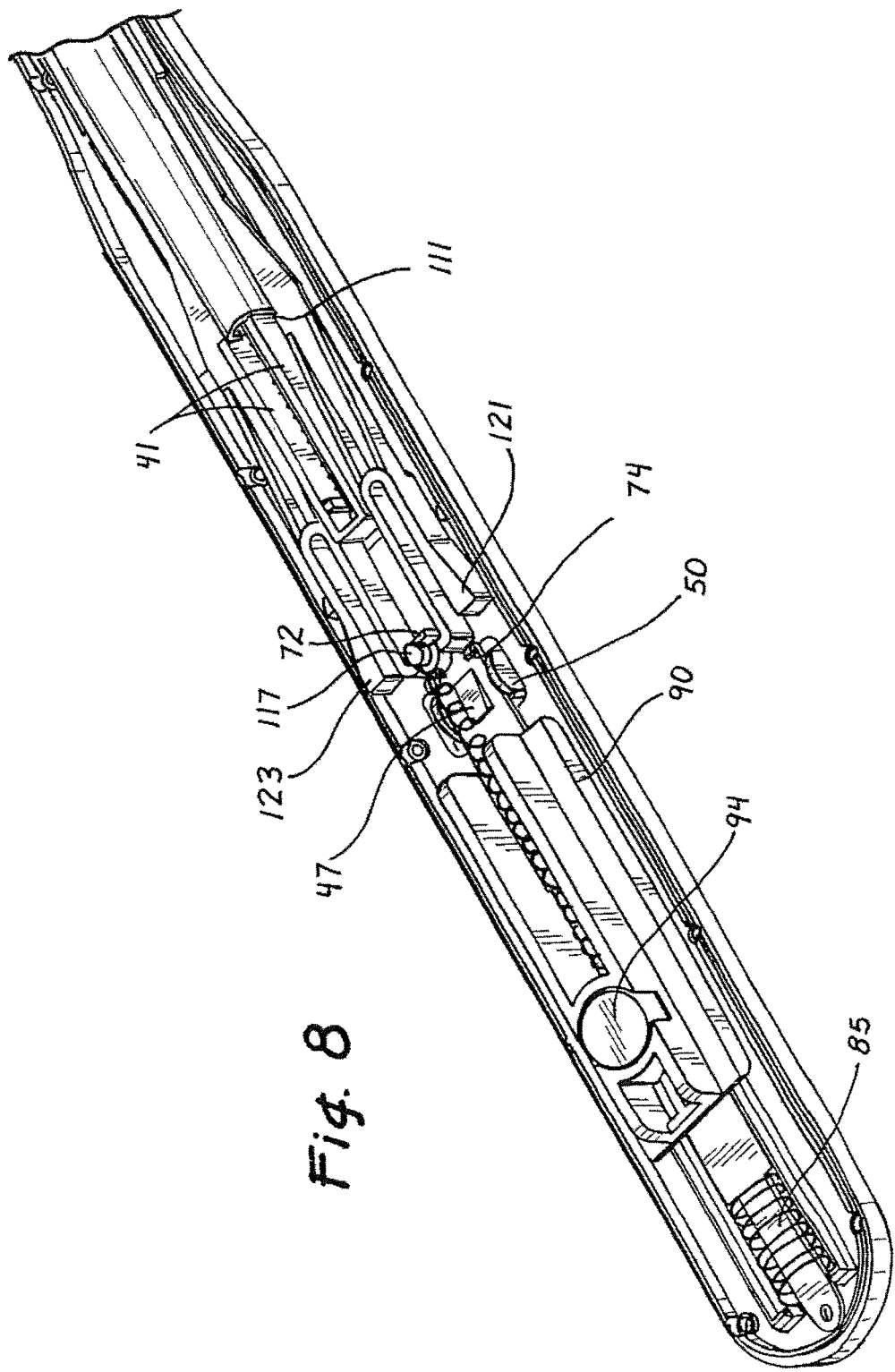
FIG. 8 is a top-side perspective view of the retractor slide block and jaw loader, each in its retracted position.
Figure 9:
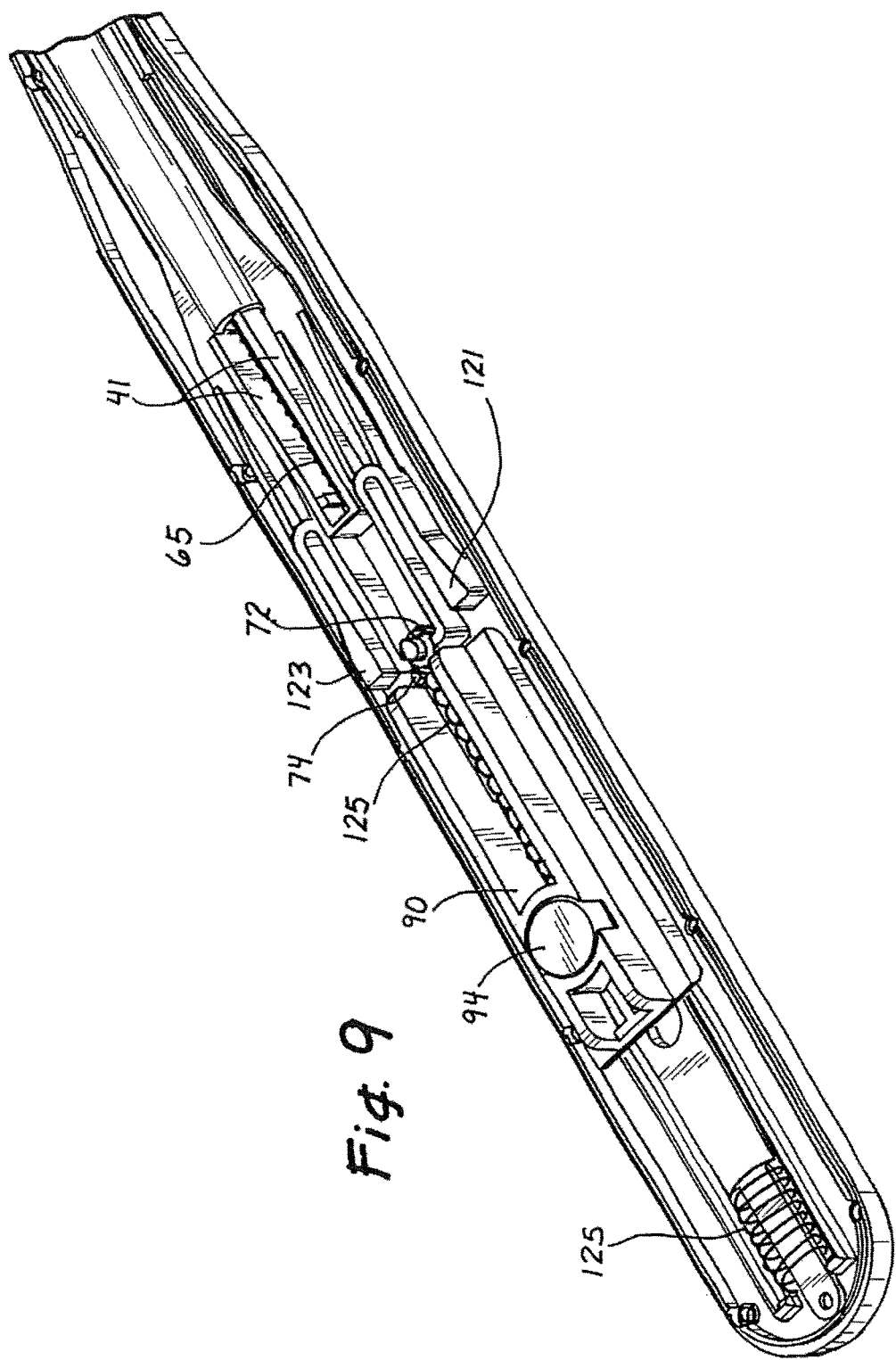
FIG. 9 is a top-side perspective view showing the retractor, slide block and jaw loader at a late stage in the closing strokes.
Figure 10:
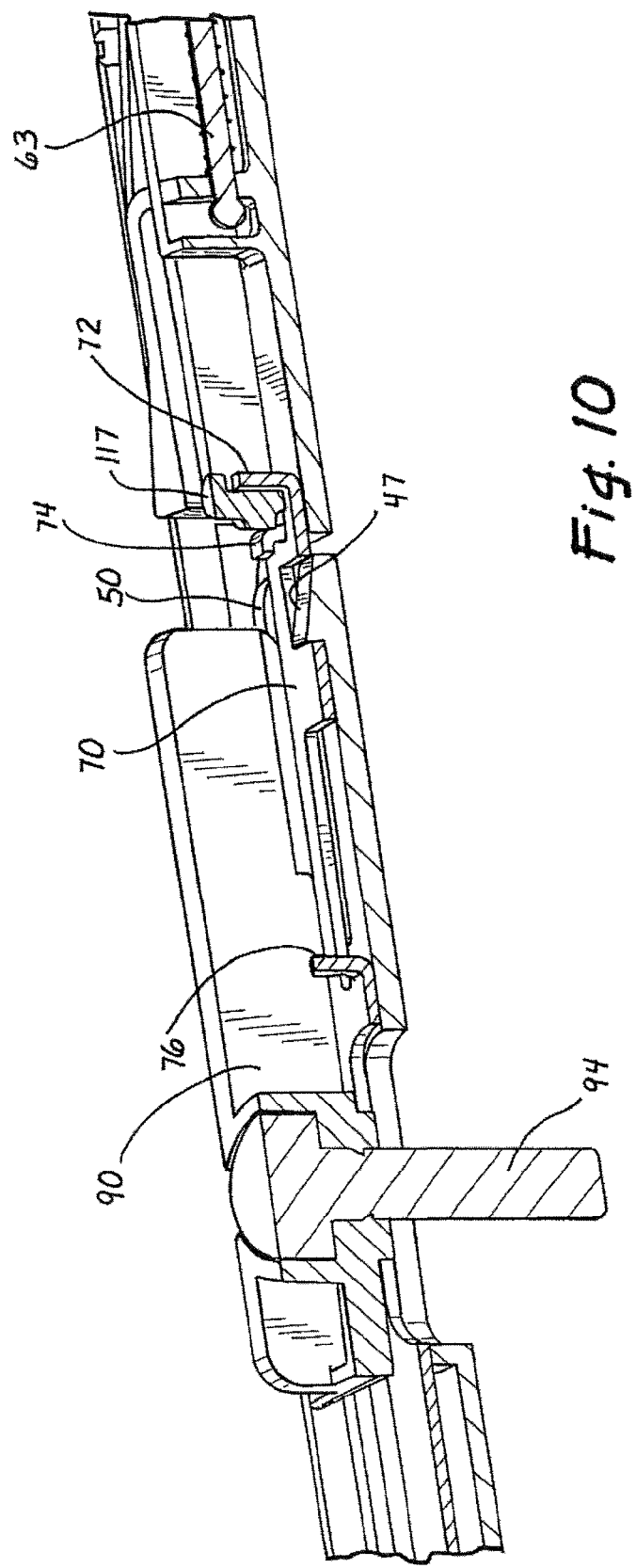
FIG. 10 is an axial cross section view of the slide block and jaw loader at the stage illustrated in FIG. 9.
Figure 11:
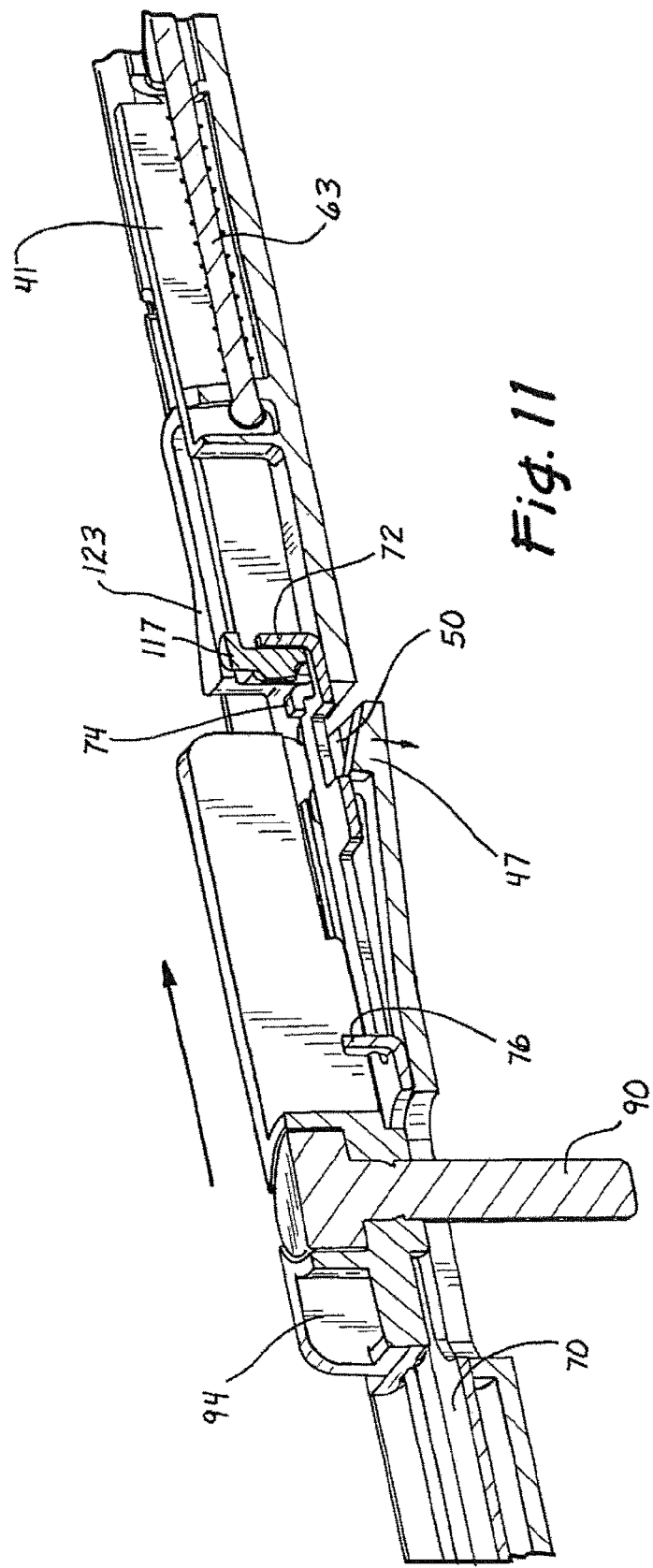
FIG. 11 is an axial cross section view similar to FIG. 10 and showing the slide block releasing a keeper to initiate advancement of the jaw loader.

The continuous and ongoing portion of this process is associated with the clip advancer 61 as illustrated in FIG. 5a. In this view, the train 59 of clips 57 is urged distally by the clip advancer 61 which in turn is biased to move distally along the rod 63 by the spring 65. This bias of the clip train 59 continues generally independently of any other function associated with the clip applier 10.

The remaining operation of the clip applier 10 is repetitive so one must pick a point in the cycle to begin this discussion. For purposes of discussion, it will be assumed that the process begins with a single clip 57 disposed in the jaws 18 at the completion of the opening stroke when the handles of the assembly 14 (FIG. 1) are maximally separated. This point is designated by the reference numeral 126 along a cycle time line 128 illustrated in FIG. 5b.

At this point in time, the jaw loader 101 is disposed at its distal most position where it extends between the jaws 18. The retraction spring 125 is fully extended or stretched while the retractor spring 85 is generally uncompressed. With the handle assembly 14 maximally opened, the drive pin 94 associated with the slide block 90 is in its distal most position.

In order to crimp the clip 57 and the jaws 18, the natural motion of the handle assembly 14 is to move the handles together. Thus begins the closing stroke at point 124 of the time line 126. As the handles of the assembly are brought into proximity, the pawls 21 push against the bias of the jaw spring 127 to close the jaws 18 and thereby crimp the clip 57.

Before the clip 57 can be crimped however, the jaw loader 101 must be removed from between the jaws 18. This is accomplished with the delay mechanism previously discussed, which responds almost immediately to the proximal movement of the drive pin 94 as shown by a point 128 in FIG. 5b. With reference to FIG. 6, it will be noted that when the drive pin 94 moves proximally the slide block 90 is carried with it along with the retractor 70. The jaw loader 101 is also moved proximally due to its engagement with the tab 72 of the retractor 70.

As this proximal movement continues, the wings 121 and 123 of the jaw loader 101 ride up on the inclined elements 52 formed in the bottom 32 of the housing. As the wings 121 and 123 ride up on the inclined elements 52, the proximal wall 115 clears the abutments 74. This causes the jaw loader 101 to snap proximally until the surface 111 associated with the tunnel 107 contacts the upstanding walls 41 of the bottom 32. Thus, at an early stage in the closing stroke, the jaw loader 101, and particularly the tongue 103, is rapidly and positively withdrawn from between the jaws 18. The remainder of the closing stroke, beginning at a point 129 for example, moves the pawls 21 against jaw 18 thereby crimping the up clip 57 to a point 130 in FIG. 5b which represents the end of the close stroke and the beginning of the open stroke. Note that approximately 90 percent of the closing stroke is devoted to the tactile feedback associated with crimping the clip 57 onto the tissue. As the handle assembly 14 continues to be closed, the drive pin 94 is drawn proximally along with the retractor 70 thereby compressing the retractor spring 85. With the jaw loader 101 stopped by the walls 41, the continued proximal movement of the slide block 90 and retractor 70 stretches the tension spring 125 to its maximum extent.

This completes the closing stroke of the process at the point 129, crimping the clip 57 onto the tissue. It is now desirable to open the jaws 18 in order to release the crimped clip, and to load a new clip 57 into the jaws 18.

In order to open the jaws 18, the normal movement of the handle assembly is to separate the handles in an opening stroke which, for a preferred embodiment, begins at the point 130 along the time line 126. At the beginning of this stroke, when the handles of the assembly 14 are initially moved apart, the drive pin 94 begins its distal movement. Approximately 95 percent of this distal movement is associated with spreading the pawls 21 so that the jaws can separate under the bias of the spring 127. As the handle assembly 14 continues to be open, the drive pin is moved distally carrying the slide block 90 into proximity with its distal most position. This point is designated by the reference numeral 131 in FIG. 5b. No other forces act on the slide block 90 until it reaches the actuators 50 associated with the keeper 47.

Figure 12:
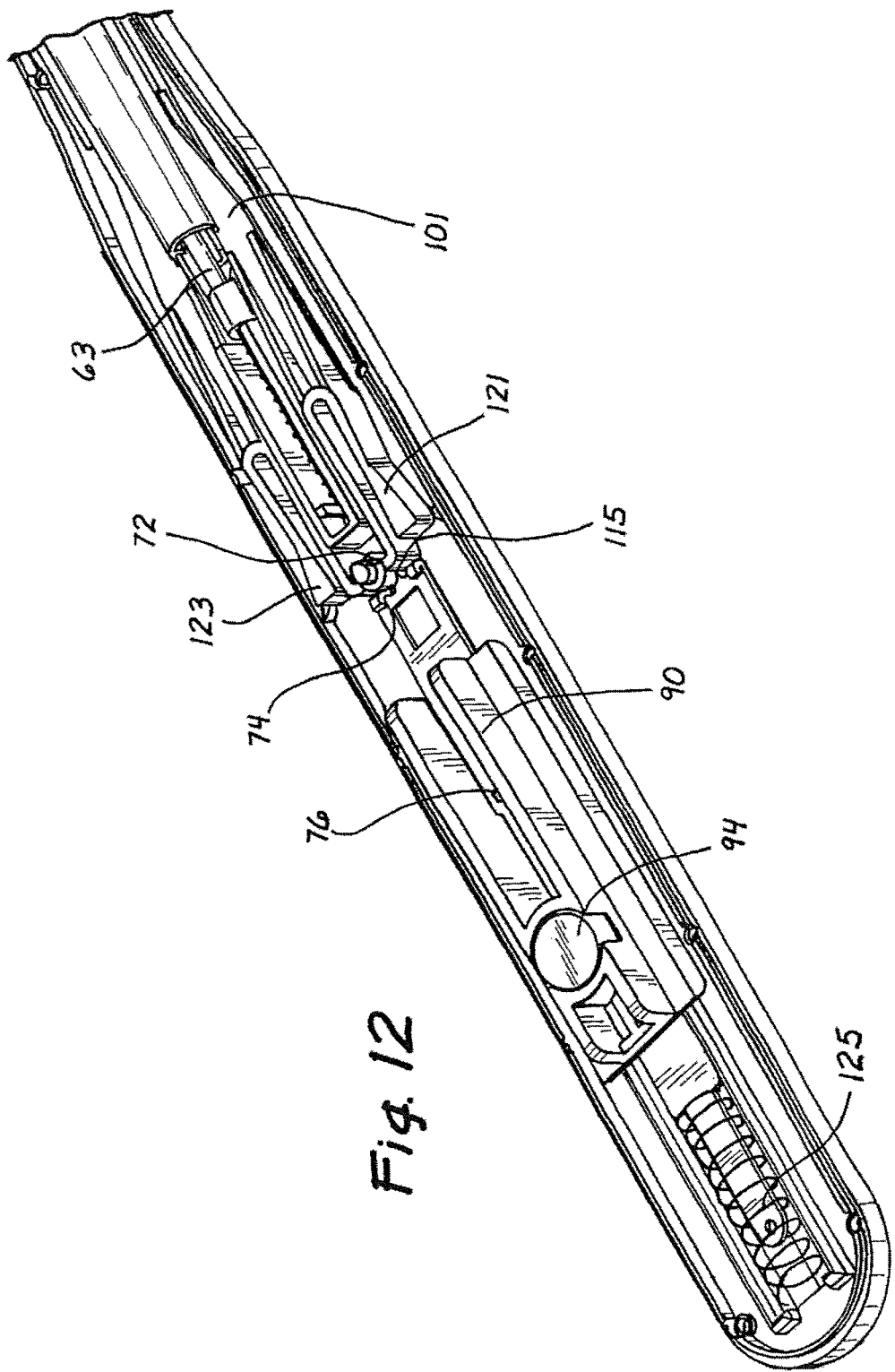
FIG. 12 is a top-side perspective view showing the slide block and jaw loader at a late stage in the opening stroke.
Figure 13:
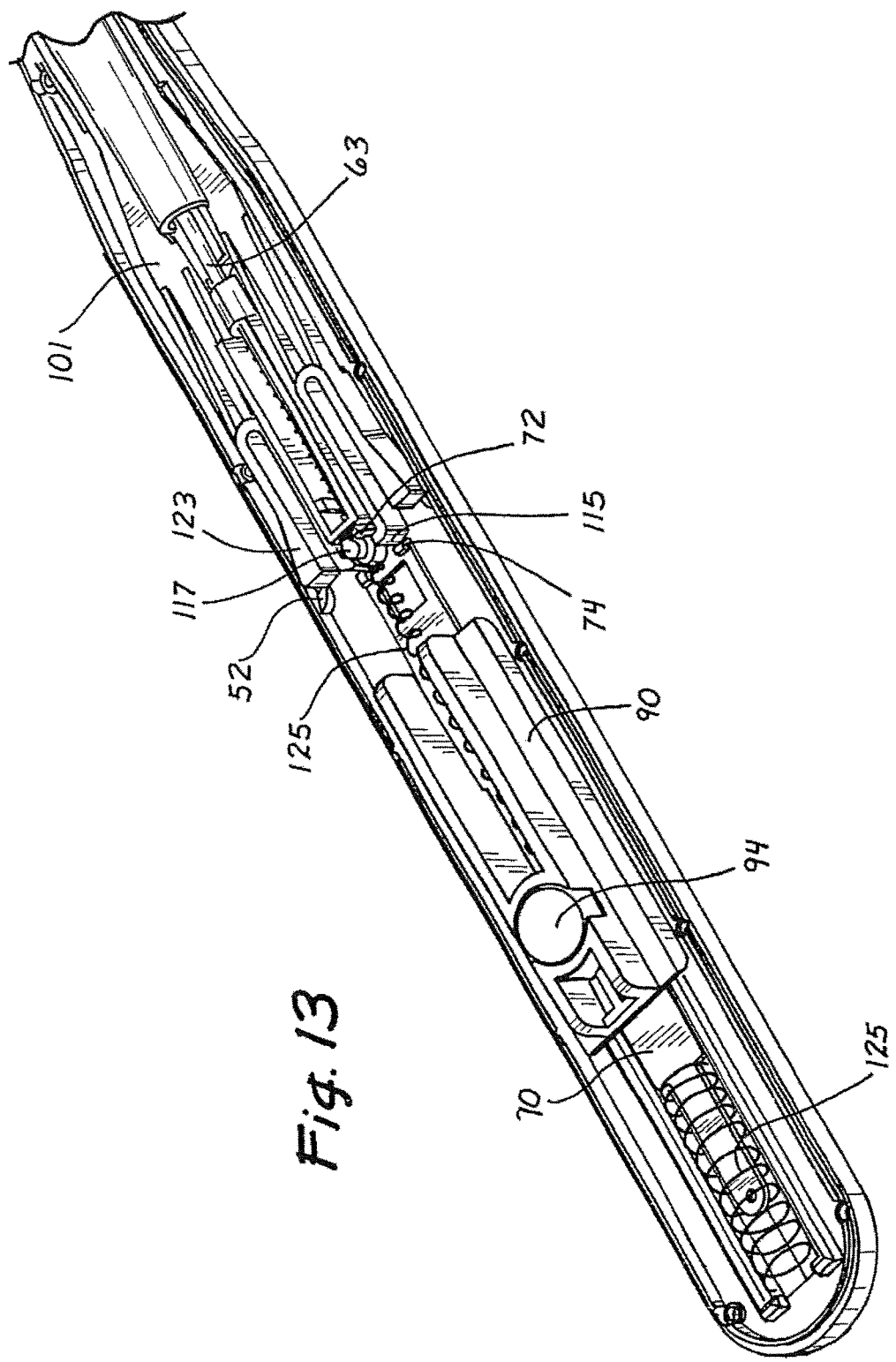
FIG. 13 is a top/slide perspective view showing the slide block and jaw loader at an ultimate stage of the opening stoke.

As the handle assembly 14 is further opened and the slide block 90 is driven further in the distal direction, the block 90 depresses the actuators 50 as well as the keeper 47. When the keeper 47 is sufficiently depressed, the retractor 70 snaps distally, causing the abutments 74 to push against the proximal wall 115, forcing the clip loader 101 to move the next clip 57 into the jaws 18. It will be noted that this movement of the next clip 57 is accomplished at the end of the open stroke in a positive and instantaneous manner. This ensures that the jaws 18 are fully open and ready to receive the next clip 57 before it is moved into position. Only then does the retractor 70 respond to the compression of the retractor spring 85 to move the jaw loader 101 against the clip. As the jaw loader 101 is snapped distally, the wings 121 and 123 are bent inwardly by the inclined elements 152 as illustrated in FIG. 12 until the wings 121, 123 clear the elements 152 as illustrated in FIG. 13. This FIG. 13 is the same as FIG. 6 reflecting that the process has been completed with a new clip 57 loaded in the jaws 18 and the clip loader 101 in its fully distal position. A point 133 on the time line 126 designates the end of the open stroke.

The points along the timeline 126 can be further defined for a preferred embodiment of the clip applier 10. In this embodiment, it will be noted that the pawls 21 of the handle assembly 14 are increasingly separated in the open stroke until they reach a space relationship. The pawls 21 are increasingly moved together in the closed stroke until they reach a fully proximate position. As noted, the jaws 18 are biased to an open state but are moveable to a closed state. In this embodiment, when the pawls 21 are in the fully spaced relationship, the jaws 18 are biased to their open state. However, in this embodiment, the pawls 21 are open further in their fully spaced relationship than the jaws 18 in their open position. As a result, the handle assembly disengages and is spaced from the pawls 21 at the end of the open stroke and the beginning of the closed stroke.

In operation, the point 124 on the timeline 126 is characterized in this embodiment by the pawls 21 in the fully spaced relationship, the jaws 18 in the open state, and the jaw loader 101 in the distal position between the jaws 18. As the closed stroke begins, the point 128 is defined by the jaws 18 in the open position, the clip between the jaws in the open state and the jaw loader 101 retracted to the proximate position. Although the pawls 21 may have begun movement toward the closed position, they have not yet engaged the jaws 18 in this particular embodiment.

At the point 129 on the timeline 126, the pawls 21 first engaged the jaws 18. Note that this point 129 follows the point 128 when the jaw loader 101 was fully retracted. Between the points 129 and 130, the pawls 21 move the jaws 18 against their normal bias to their closed or fully proximate relationship. This of course, causes the clip 57 to be crimped. If it is desired that the clip 57 be left in a less than fully crimped state, the jaw assembly 14 can be reversed between the points 129 and 130 to disengage the clip 57 at its less than fully crimped state. With the clip applier 10 removed from the operative site, the handle assembly 14 can close to the point 130 wherein the pawls 21 are at their fully proximate relationship and the jaws 18 are in their closed position.

As the open stroke begins at the point 130, the pawls 21 begin to spread, permitting the jaws 18 to separate under their own bias toward the open position. Eventually, the jaws 18 reach their fully open position, for example, at the point 131. Immediately following the point 131, the pawls 21 disengage the jaws 18. In the remainder of the open stroke, the jaw loader 101 moves distally pushing before it the next clip in the train 59.

Figure 14:
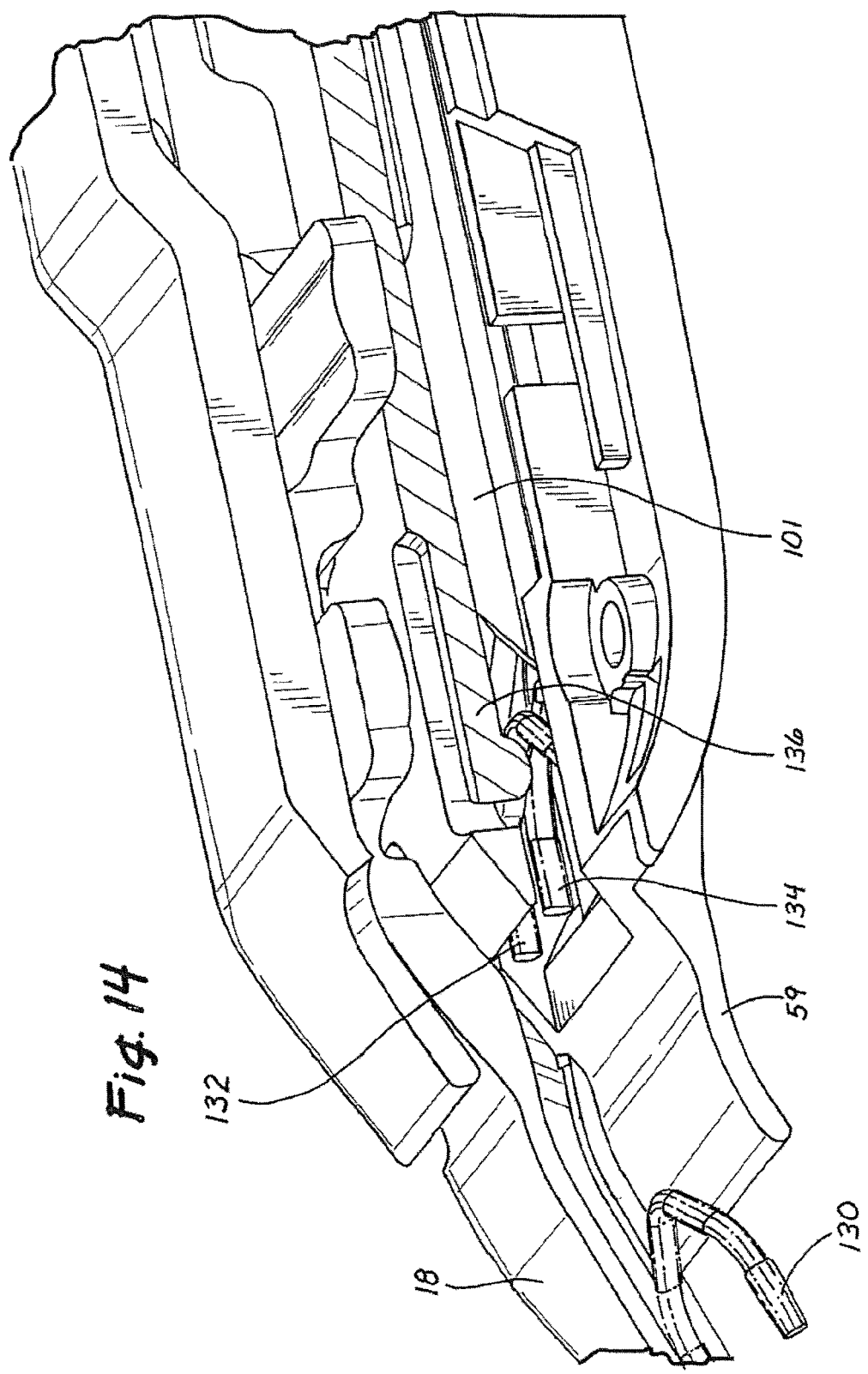
FIG. 14 is a perspective view of a clip loading arrangement including a clip staging position.

Another aspect of the present invention is associated with operation of the clips 57 in the train 59. As noted, a continuous distal pressure is asserted on the back of the train 59 biasing the clips 57, by operation of the spring 65, in the distal direction. This moves the distal most clip in the train 59 to a staging position where it is 1) elevated above the plane of the clip train 59. This is illustrated in greatest detail in FIG. 14 which shows a clip 130 loaded in the jaws 18, 2) a clip 132 disposed in the elevated staging position above the train 59, and 3) a clip 134, the ultimate clip in the train 59. When the clip 130 leaves the jaws 18, and the clip 132 advances into the jaws 18 and the clip 134 moves into the staging position. In the staging position, the clip 132 is held by a detent 137 which is then elevated by the jaw loader 101 releasing the clip 132 and snapping the clip 132 into the jaws 18.

Figure 15:
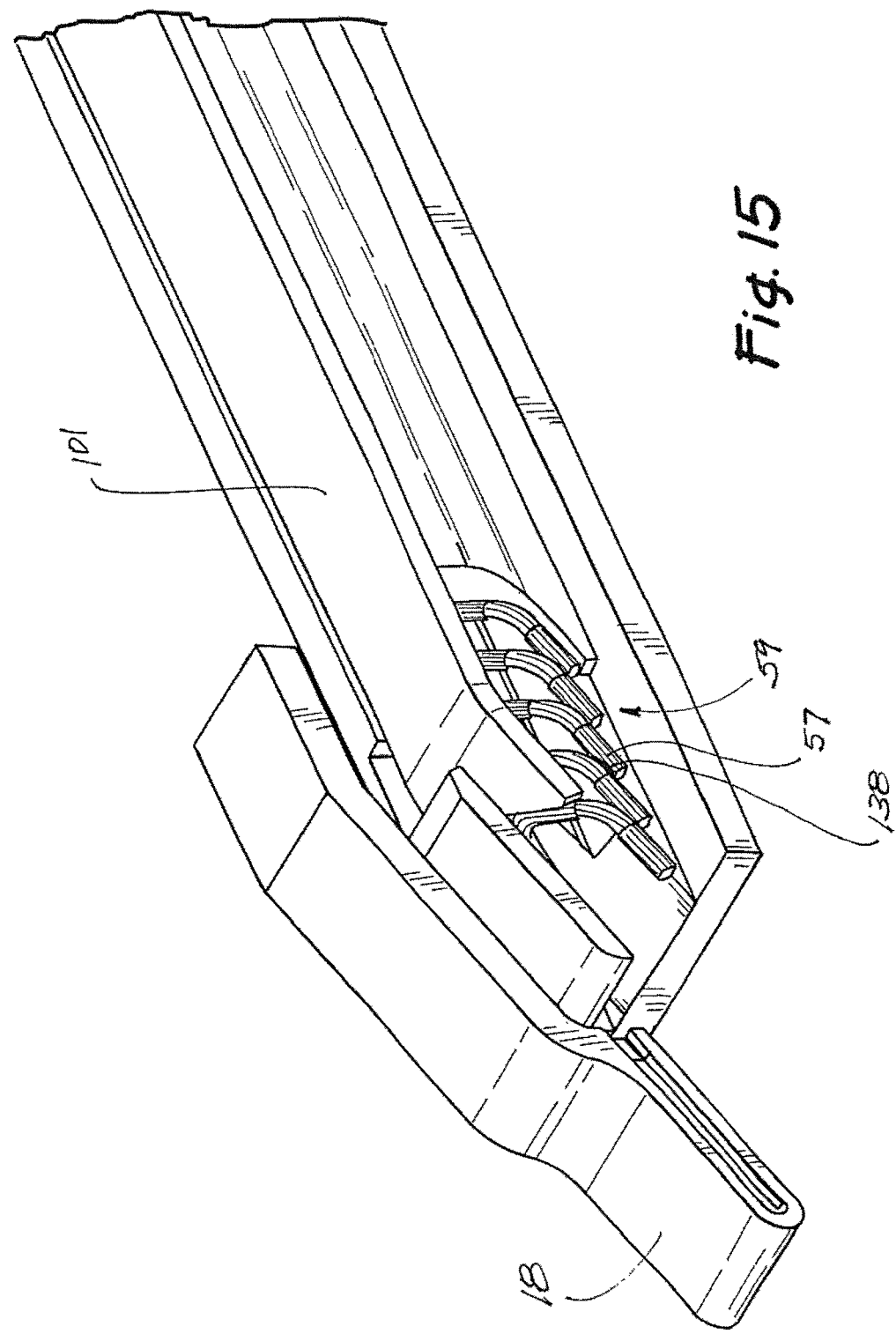
FIG. 15 is a perspective view of a further embodiment of a clip loading arrangement.

In a similar arrangement illustrated in FIG. 15, the clip train 59 is formed by clips 57 which are disposed in respective parallel planes. In this arrangement the clip loader 101 operates directly on the ultimate clip 57 to move that clip directly from the train 59 into the jaws 18. In this case, the clips 57 forming the train 59 can be joined by glue 138 as illustrated in FIG. 15.

It will be understood that many other modifications can be made to the various disclosed embodiments without departing from the spirit and scope of the concept. For example, various sizes of the surgical device are contemplated as well as various types of constructions and materials. It will also be apparent that many modifications can be made to the configuration of parts as well as their interaction. For these reasons, the above description should not be construed as limiting the invention, but should be interpreted as merely exemplary of preferred embodiments. Those skilled in the art will envision other modifications within the scope and spirit of the present invention as defined by the following claims.

The invention claimed is:

1. A surgical clip applier comprising:
    a housing extending generally longitudinally from a proximal end to a distal end, the housing comprising a clip channel extending generally longitudinally therein;
    a clip train comprising a plurality of clips positioned in the clip channel;
    a handle assembly having an open position and a closed position, and the handle assembly movable in a closing stroke from the open position to the closed position and in an opening stroke from the closed position to the open position, and the handle assembly positioned at the proximal end of the housing;
    a jaw assembly comprising a first jaw and a second jaw, the jaw assembly positioned at the distal end of the housing;
    a clip advancement mechanism configured to continuously and independently advance the clip train distally with respect to the housing;
    a delay mechanism operatively coupled to the handle assembly for loading a distal-most clip of the clip train into the jaw assembly, the delay mechanism comprising:
        a slide block slidably positioned within the housing and operatively coupled to the handle assembly such that the slide block is translated proximally during the closing stroke and is translated distally during the opening stroke;
        a retractor slidably positioned within the housing and biased longitudinally distally with respect to the housing, the retractor operatively coupled to the slide block such that the retractor is translated proximally to a proximal position during the closing stroke;
        a jaw loader slidably positioned within the housing, the jaw loader having a distal end configured to engage the distal-most clip of the clip train, the jaw loader operatively coupled to the slide block such that proximal translation of the slide block during the closing stroke tends to translate the jaw loader proximally, and operatively coupled to the retractor such that distal translation of the retractor during the opening stroke advances the jaw loader distally; and a compression spring positioned within the housing between the housing and the retractor such that the retractor is biased distally with respect to the housing by the compression spring.

2. The surgical clip applier of claim 1, wherein the delay mechanism further comprises a latch to retain the retractor in the proximal position upon completion of the closing stroke, the latch releasable during distal translation of the slide block during the opening stroke.

3. The surgical clip applier of claim 2, wherein the latch comprises:
a keeper formed in the housing and engageable with the retractor in the proximal position; and
at least one actuator actuatable by the slide block to depress the keeper.

4. The surgical clip applier of claim 1, wherein the jaw loader is operatively coupled to the retractor by a tension spring.

5. The surgical clip applier of claim 1, wherein the retractor comprises an abutment engageable with the jaw loader during the opening stroke.

6. The surgical clip applier of claim 1, wherein the housing comprises an inclined tab and wherein the jaw loader comprises a wing positioned on the inclined tab with the handle assembly in the open position and the wing advanceable over the inclined tab during the closing stroke.

7. The surgical clip applier of claim 1, wherein the jaw loader comprises a distally extending tongue, and wherein the jaw loader is positionable in a distal most position such that the distally extending tongue in of the jaw loader extends between the first and second jaws.

8. The surgical clip applier of claim 7, wherein the housing comprises an upstanding wall extending therefrom and wherein the jaw loader comprises a proximal surface that contacts the upstanding wall of the housing when the jaw loader is moved proximally to a withdrawn position in which the tongue is withdrawn from between the first and second jaws.

9. The surgical clip applier of claim 1, wherein the retractor comprises a tongue extending from a pair of shoulders and wherein the compression spring is mounted on the tongue and applies compression force to the pair of shoulders.

10. The surgical clip applier of claim 1, wherein the clip advancement mechanism comprises:
a rod seated with respect to the housing;
a clip advancer slidable along the rod; and
a spring biasing the clip advancer distally along the rod.

11. The surgical clip applier of claim 10, wherein the jaw loader comprises a tunnel formed therein, and wherein the rod of the clip advancement mechanism extends through the tunnel.

12. A surgical clip applier comprising:
a housing extending generally longitudinally from a proximal end to a distal end, the housing comprising a clip channel extending generally longitudinally therein;
a clip train comprising a plurality of clips positioned in the clip channel;
a handle assembly having an open position and a closed position, and the handle assembly movable in a closing stroke from the open position to the closed position and in an opening stroke from the closed position to the open position, and the handle assembly positioned at the proximal end of the housing;
a jaw assembly comprising a first jaw and a second jaw, the jaw assembly positioned at the distal end of the housing;
a clip advancement mechanism configured to continuously and independently advance the clip train distally with respect to the housing;
a delay mechanism operatively coupled to the handle assembly for loading a distal-most clip of the clip train into the jaw assembly, the delay mechanism comprising:
a slide block slidably positioned within the housing and operatively coupled to the handle assembly such that the slide block is translated proximally during the closing stroke and is translated distally during the opening stroke;
a retractor slidably positioned within the housing and biased longitudinally distally with respect to the housing, the retractor operatively coupled to the slide block such that the retractor is translated proximally to a proximal position during the closing stroke; and
a jaw loader slidably positioned within the housing, the jaw loader having a distal end configured to engage the distal-most clip of the clip train, the jaw loader operatively coupled to the slide block such that proximal translation of the slide block during the closing stroke tends to translate the jaw loader proximally, and operatively coupled to the retractor such that distal translation of the retractor during the opening stroke advances the jaw loader distally; and
wherein the handle assembly has a scissor configuration such that the handle assembly comprises a first handle pivotally connected to a second handle.

13. The surgical clip applier of claim 12, wherein the handle assembly comprises:
a first slot movable by the first handle;
a second slot movable by the second handle and converging with the first slot; and
a button positioned within the converging slots and movable between a distal position at an end of the opening stroke and a proximal position at an end of the closing stroke; and
wherein the slide block comprises a drive pin engageable in the button.

14. A surgical clip applier comprising:
a housing extending generally longitudinally from a proximal end to a distal end, the housing comprising a clip channel extending generally longitudinally therein;
a clip train comprising a plurality of clips positioned in the clip channel;
a handle assembly movable in a closing stroke and an opening stroke, the handle assembly disposed at the proximal end of the housing;
a jaw assembly comprising a first jaw and a second jaw, the jaw assembly positioned at the distal end of the housing, the jaw assembly actuatable by the handle assembly between an open state in which the first jaw is spaced from the second jaw to receive a distal-most clip of the plurality of clips therebetween and a closed state in which the first jaw and the second jaw are positioned proximate one another to crimp the clip positioned therebetween;
a delay mechanism positioned within the housing for loading the distal-most clip of the plurality of clips into the jaw assembly, the delay mechanism comprising:
a slide block slidably positioned within the housing and operatively coupled to the handle assembly to slide proximally during the closing stroke and slide distally during the opening stroke;

a jaw loader slidably positioned within the housing, the jaw loader having a distal end configured to engage the distal-most clip of the clip train, the jaw loader slidable to a distal-most position with the jaw assembly in the open state in which the distal end of the jaw loader is positioned between the first jaw and the second jaw to load the distal-most clip into the jaw assembly; and a tension spring coupling the jaw loader to the slide block, the tension spring fully extended at the end of the opening stroke of the handle assembly and configured to rapidly withdraw the jaw loader proximally during the closing stroke of the handle assembly; and wherein the closing stroke of the handle assembly comprises:

an initial removal stage in which the jaw loader is rapidly slid proximally such that the distal end of the jaw loader is removed from between the first jaw and the second jaw of the jaw assembly by the tension spring wherein the handle assembly is disengaged from jaw assembly during the removal stage such that the jaw assembly is not actuated during the removal stage; and a subsequent feedback stage in which the handle assembly is operatively coupled to the jaw assembly such that tactile feedback of crimping the clip positioned between the first and second jaws is transmitted to the handle assembly.

15. The surgical clip applier of claim 14, wherein the feedback stage comprises approximately 90% of the opening stroke.

16. The surgical clip applier of claim 14, wherein the removal stage comprises approximately 5% of the opening stroke.

17. The surgical clip applier of claim 14, wherein the opening stroke of the handle assembly comprises:

an opening stage in which the jaw assembly is moved from the closed state to the open state; and a loading stage in which the jaw loader is slid to the distal most position to load the distal-most clip of the clip train into the jaw assembly.

\* \* \* \* \*